United States Patent
Makkiabadi et al.

(10) Patent No.: US 11,471,667 B2
(45) Date of Patent: Oct. 18, 2022

(54) ELECTRICAL STIMULATION OF A BRAIN

(71) Applicants: Bahador Makkiabadi, Tehran (IR); Ahmadreza Mohammadzadeh Ghomian, Tehran (IR)

(72) Inventors: Bahador Makkiabadi, Tehran (IR); Ahmadreza Mohammadzadeh Ghomian, Tehran (IR)

(73) Assignee: Bahador Makkiabadi, Tehran (IR)

( * ) Notice: Subject to any disclaimer, the term of this patent is extended or adjusted under 35 U.S.C. 154(b) by 394 days.

(21) Appl. No.: 16/038,292

(22) Filed: Jul. 18, 2018

(65) Prior Publication Data

US 2018/0318574 A1    Nov. 8, 2018

Related U.S. Application Data

(60) Provisional application No. 62/533,676, filed on Jul. 18, 2017.

(51) Int. Cl.
| | |
|---|---|
| *A61N 1/04* | (2006.01) |
| *A61B 5/00* | (2006.01) |
| *A61N 1/36* | (2006.01) |
| *A61B 5/30* | (2021.01) |
| *A61B 5/291* | (2021.01) |
| *A61B 5/316* | (2021.01) |
| *A61B 5/377* | (2021.01) |

(52) U.S. Cl.
CPC ............ *A61N 1/0456* (2013.01); *A61B 5/291* (2021.01); *A61B 5/30* (2021.01); *A61B 5/316* (2021.01); *A61B 5/377* (2021.01); *A61B 5/4064* (2013.01); *A61B 5/7207* (2013.01); *A61B 5/7225* (2013.01); *A61N 1/3603* (2017.08); *A61N 1/36025* (2013.01); *A61B 2560/0443* (2013.01)

(58) Field of Classification Search
None
See application file for complete search history.

(56) References Cited

U.S. PATENT DOCUMENTS

| | | | |
|---|---|---|---|
| 2008/0046023 A1* | 2/2008 | Fischell | A61N 1/36185 607/45 |
| 2017/0224990 A1* | 8/2017 | Goldwasser | A61N 1/0456 |
| 2018/0304076 A1* | 10/2018 | Lehmann | A61N 1/36038 |
| 2019/0282817 A1* | 9/2019 | Muller | A61B 5/0478 |

* cited by examiner

*Primary Examiner* — Erica S Lee
(74) *Attorney, Agent, or Firm* — Bajwa IP Law Firm; Haris Zaheer Bajwa (57) ABSTRACT

A circuit for electrical stimulation of a brain is disclosed. The circuit may include a plurality of electrical stimulators, a plurality of electrodes, a crossbar switch, and a processing unit. Each of the plurality of electrical stimulators is configured to generate an electrical signal. The crossbar switch includes a plurality of individual switches. The processing unit is configured to provide a connection between at least one of the plurality of electrical stimulators and a first electrode of the plurality of electrodes through an individual switch of the plurality of individual switches by turning on the individual switch.

8 Claims, 6 Drawing Sheets

ELECTRICAL STIMULATION OF A BRAIN

CROSS-REFERENCE TO RELATED APPLICATION

This application claims the benefit of priority from U.S. Provisional Patent Application Ser. No. 62/533,676, filed on Jul. 18, 2017, and entitled "A SYSTEM FOR ELECTRICAL STIMULATION OF BRAIN," which is incorporated herein by reference in its entirety.

TECHNICAL FIELD

The present disclosure generally relates to brain stimulation, and particularly to a modular electrical system for stimulation of brain with simultaneous electroencephalography (EEG) recording and electrical impedance tomography (EIT) imaging.

BACKGROUND

Transcranial direct current stimulation (tDCS) is a non-invasive brain stimulation method that can be used in cognitive and clinical protocols in order to modulate neural activity. Although some macro effects are known, the underlying mechanisms are still not clear. tDCS in combination with electroencephalography (EEG) can lead to understanding these mechanisms from a neural point of view. However, simultaneous tDCS-EEG still remains challenging because of the artifacts that affect the recorded signals. For example, simultaneous EEG recording using the electrical brain stimulation may increase the possibility of saturation of EEG electrodes within the range of stimulating electrodes (anode or cathode).

The after-effects of tDCS on both motor and cognitive performances is a potential for using tDCS in a variety of clinical applications. However, little is known about the real-time effects of tDCS on rhythmic cortical activity in humans due to technical challenges of simultaneously obtaining electrophysiological data during ongoing stimulations. There is, therefore, a need for a device that simultaneously acquires electrophysiological data during brain stimulation using high-resolution EEG.

SUMMARY

This summary is intended to provide an overview of the subject matter of the present disclosure, and is not intended to identify essential elements or key elements of the subject matter, nor is it intended to be used to determine the scope of the claimed embodiments. The proper scope of the present disclosure may be ascertained from the claims set forth below in view of the detailed description below and the drawings.

According to one or more exemplary embodiments, the present disclosure is directed to a circuit for electrical stimulation of a brain. The exemplary circuit may include a plurality of electrical stimulators, a plurality of electrodes, a crossbar switch, and a processing unit. Each of the plurality of electrical stimulators may be configured to generate an electrical signal. The crossbar switch may include a plurality of individual switches. The processing unit may be configured to provide a connection between at least one of the plurality of electrical stimulators and a first electrode of the plurality of electrodes through an individual switch of the plurality of individual switches by turning on the individual switch.

In an exemplary embodiment, the circuit may further include a plurality of transceiver modules. The plurality of transceiver modules may include a first transceiver module. In an exemplary embodiment, the first transceiver module may include an input node P1, an input node P2, and an output node O1. Input node P1 may be connected to a second electrode of the plurality of electrodes. Input node P2 may be connected to a third electrode of the plurality of electrodes. Output node O1 may be connected to the processing unit. In an exemplary embodiment, the processing unit may be configured to control data transfer through the plurality of transceiver modules. The transceiver module may be configured to receive data from the second electrode and the third electrode. In another embodiment, the first electrode may be the same as the second electrode.

In an exemplary embodiment, the circuit may further include an adder module. The adder module may be configured to receive data from an output node DRL1 of the first transceiver module and receive data from an output node DRL2 of a second transceiver module of the plurality of transceiver modules. In an embodiment, a sum of data on output node DRL1 and data on output node DRL2 may be loaded to an output node of the adder module.

In an exemplary embodiment, the first transceiver module may further include a DC canceller module, an echo canceller module, a first band-pass filter, a second band-pass filter, a differential amplifier, an amplifier, an anti-aliasing filter, an analog-to-digital converter (ADC), and an output node OUT. In an exemplary embodiment, the DC canceller module may be connected to input node P1 through a buffer B2 and a switch S1. Switch S1 may be controlled by the processing unit. The DC canceller module may be configured to suppress DC data of input node P1. In an embodiment, the echo canceller module may be connected to input node P1 through a buffer B3 and a switch S2. Switch S2 may be controlled by the processing unit. The echo canceller module may be configured to suppress echoes of AC data of the input node P1. In an exemplary embodiment, the first band-pass filter may be connected to input node P1 through a buffer B1 and a switch S10. Switch S10 may be controlled by the processing unit. Outputs of the DC canceller module and the echo canceller module may be connected to an input node of the band-pass filter. In an exemplary embodiment, the second band-pass filter may be connected to input node P2 through a switch S11. Switch S11 may be controlled by the processing unit. In an exemplary embodiment, the differential amplifier may include a first differential input node, a second differential input node, a differential output node, and a differential ground node. In an embodiment, the first differential input node may be connected to an output of the first band-pass filter. The second differential input node may be connected to an output of the second band-pass filter. The differential ground node may be connected to an output node DRL1. In an exemplary embodiment, the differential amplifier may be configured to load an amplification of a difference between data on the first differential input node and data on the second differential input node to the differential output node. In an embodiment, the amplifier may be configured to amplify data of the differential output node. The anti-aliasing filter may be connected to the amplifier output. The analog-to-digital converter (ADC) may be connected to an output of the anti-aliasing filter. Output node OUT may be connected to an output of the ADC.

In an exemplary embodiment, an electrical stimulator of the plurality of electrical stimulators may include a power supply, a digital to analog converter (DAC), a current source, a voltage source, a node X1, and a node X2. In an embodiment, the DAC may be configured to generate an amplitude and a frequency of the electrical signal. The current source may be connected to an output node of the DAC. The voltage source may be connected to the output node of the DAC. Node X1 may be connected to the current source through a voltage/current limiter and a switch SB1, and may be connected to the voltage source through the voltage/current limiter and a switch SB2. In an exemplary embodiment, the voltage/current limiter and switches SB1 and SB2 may be controlled by the processing unit. Node X2 may be connected to the power supply.

In an exemplary embodiment, the processing unit may be configured to provide a digital amplitude and a digital frequency of the electrical signal to the DAC. In an exemplary embodiment, the power supply may include an isolated DC power supply.

In an exemplary embodiment, the electrical stimulator may further include a digital data isolator. The digital data isolator may be configured by the processing unit to provide a digital amplitude and a digital frequency of the electrical signal to the DAC.

In an exemplary embodiment, the circuit may further include an amplification module. The amplification module may include a filter, an amplifier, and analog to digital converter (ADC). In an exemplary embodiment, the filter, the amplifier, and the ADC may be connected in series. The amplification module may be configured to provide a path between the first electrode and an input of the processing unit.

In an exemplary embodiment, the processing unit may be further configured to calculate an electrical impedance by measuring voltage and current values of the first electrode through the amplification module. In an embodiment, the plurality of electrodes may include an electroencephalography (EEG) electrode connected to a head of a patient.

In another general aspect, the present disclosure is directed to a circuit for electrical stimulation of a brain. The circuit includes a differential amplifier, an electrical stimulator, and a processing unit. In an embodiment, the differential amplifier may be configured to amplify a difference between data on a node P1 and a node P2. The electrical stimulator may be configured to load an electrical signal on node P1. The processing unit may be configured to generate an amplitude and a frequency of the electrical signal. In an exemplary embodiment, node P1 may be connected to a first electrode of a plurality of electrodes.

In an exemplary embodiment, the electrical stimulator may include a first digital to analog converter (DAC), a main current source, a current dependent voltage source, a second digital to analog converter (DAC), an auxiliary current source, and an adder unit. In an embodiment, the first DAC may be configured to receive a first pair of digital values for the amplitude and the frequency from the processing unit, and convert the first pair of digital values to a first pair of analog values. The main current source may be configured to generate a main electric current according to the first pair of analog values. The current dependent voltage source may be connected to the main current source through a switch S7. Switch S7 may be controlled by the processing unit. The second DAC may be configured to receive a second pair of digital values for the amplitude and the frequency from the processing unit, and convert the second pair of digital values to a second pair of analog values. The auxiliary current source may be configured to generate an auxiliary electric current according to the second pair of analog values. In an exemplary embodiment, the adder unit may include a first adder input, a second adder input, and an adder output. The first adder input may be connected to the main current source through a switch S8. Switch S8 may be controlled by the processing unit. The second adder input may be connected to the auxiliary current source through a switch S9. Switch S9 may be controlled by the processing unit. In an exemplary embodiment, the adder unit may be configured to load a sum of the first adder input and the second adder input to the adder output. The main current source may be connected to the processing unit through the first DAC and a first filter. The auxiliary current source may be connected to the processing unit through the second DAC and a second filter. An output of the current dependent voltage source may be connected to node P1 through a switch S3 and a voltage/current limiter. Switch S3 and the voltage/current limiter may be controlled by the processing unit. The adder output may be connected to node P1 through a switch S4 and the voltage/current limiter. Switch S4 may be controlled by the processing unit. An output of the auxiliary current source may be connected to node P1 through a switch S5 and the voltage/current limiter. Switch S5 may be controlled by the processing unit.

In an embodiment, the circuit may further include a DC canceller module, an echo canceller module, a band-pass filter, a first amplifier, an anti-aliasing filter, and a first analog-to-digital converter (ADC). In an exemplary embodiment, the DC canceller module may be connected to input node P1 through a buffer B2 and a switch S1. Switch S1 may be controlled by the processing unit. The DC canceller module may be configured to suppress DC data of input node P1. In an embodiment, the echo canceller module may be connected to input node P1 through a buffer B3 and a switch S2. Switch S2 may be controlled by the processing unit. The echo canceller module may be configured by the processing unit to suppress echoes of AC data of input node P1. In an exemplary embodiment, the band-pass filter may be connected to input node P1 through a buffer B1 and a switch S10. Switch S10 may be controlled by the processing unit. Outputs of the DC canceller module and the echo canceller module may be connected to an input node of the band-pass filter. An output of the band-pass filter may be connected to a first differential input node of the differential amplifier. The first amplifier may be configured to amplify an output of the differential amplifier. The anti-aliasing filter may be connected to the amplifier output. The first ADC may be connected to an output of the anti-aliasing filter. An output of the first ADC may be loaded to the processing unit.

In an exemplary embodiment, the processing unit may be further configured to receive voltage and current values of the first electrode from node P1 through a voltage/current limiter, a switch S6, a third filter, a second amplifier, and a second analog-to-digital converter (ADC), and calculate an electrical impedance by processing the voltage and the current values of the first electrode.

In an embodiment, the processing unit may be further configured to generate a high voltage by a high-voltage generator module, and load the high voltage on node P1 through a switch S12. Switch S12 may be controlled by the processing unit.

In an exemplary embodiment, the differential amplifier may include an instrumentation amplifier. A ground node of the instrumentation amplifier may be connected to a drive right leg (DRL) circuit.

In an embodiment, node P2 may be connected to a second electrode of the plurality of electrodes through a switch S11. Switch S11 may be controlled by the processing unit. The plurality of electrodes may include an electroencephalography (EEG) electrode connected to a head of a patient.

In another general aspect, the present disclosure describes an exemplary method for electrical stimulation of a brain. The method may include injecting an electric current into the brain through a first electrode of a plurality of electrodes, measuring a voltage difference between a pair of electrodes of the plurality of electrodes by a transceiver module, obtaining a an electrical impedance map of the brain by an electrical impedance tomography (EIT) imaging process, positioning a second electrode of the plurality of electrodes on the head of the patient according to the electrical impedance map, injecting an electrical signal to the second electrode by an electrical stimulator, and measuring a voltage of the second electrode by the transceiver module. The plurality of electrodes may be placed on a head of a patient. The electric current may be generated by an electrical stimulator. The transceiver module may configured to receive data from the pair of electrodes. The electric current and the voltage difference may be used as boundary values in the EIT imaging process. Injecting the electrical signal and measuring the voltage may be performed simultaneously.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the claims herein.

BRIEF DESCRIPTION OF THE DRAWINGS

The drawing figures depict one or more embodiments in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary embodiments will be readily apparent to one skilled in the art, and the general principles defined herein may be applied to other embodiments and applications without departing from the scope of the present disclosure. The present disclosure is not intended to be limited to the embodiments shown, but is to be accorded the widest possible scope consistent with the principles and features disclosed herein.

Disclosed systems and techniques are directed to an exemplary circuit and exemplary method for electrical stimulation of brain. The circuit may include a number of electrical stimulators that generate electric current/voltage. The electric current/voltage may be injected to one or more of electrodes that are place on the head of a patient. Simultaneously, electroencephalography (EEG) signals may be recorded via the same electrodes by a number of transceiver modules. The transceiver modules may also measure the electrical impedance distribution of the head by utilizing the electrical stimulators to inject electric current to the head boundaries via different pairs of electrodes placed on the head, and may perform an electrical impedance tomography (EIT) imaging process by a processing unit. The impedance distribution may be used to find modified positioning of electrodes for an improved electrical stimulation of the head.

Figure 1:
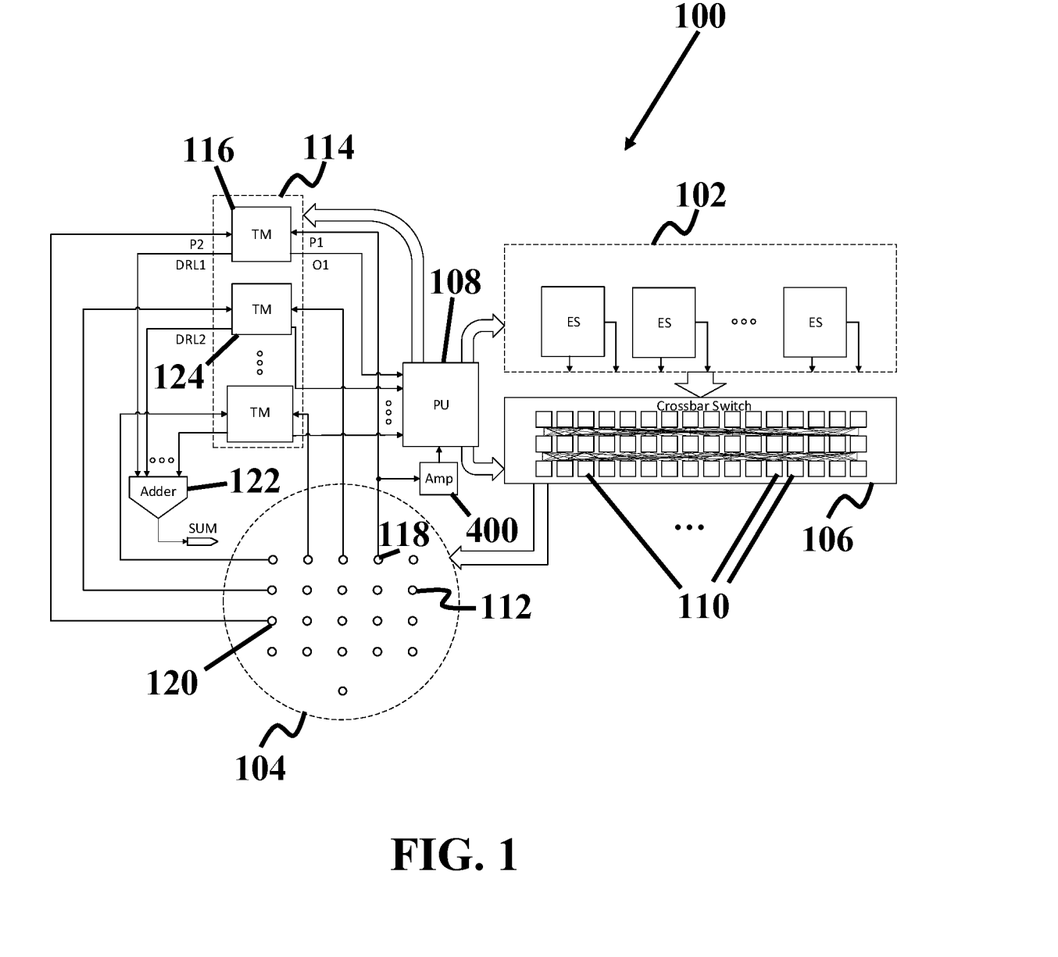
FIG. 1 shows a schematic of a circuit for electrical stimulation of brain, consistent with one or more embodiments of the present disclosure.

FIG. 1 shows a schematic of a circuit 100 for electrical stimulation of a brain, consistent with one or more embodiments of the present disclosure. Circuit 100 may include a plurality of electrical stimulators 102, a plurality of electrodes 104, a crossbar switch 106, and a processing unit 108. Each of plurality of electrical stimulators 102 may be configured to generate an electrical signal. Crossbar switch 106 may include a plurality of individual switches 110. Processing unit 108 may be configured to provide a connection between at least one of plurality of electrical stimulators 102 and a first electrode 112 of plurality of electrodes 104 through a respective individual switch of plurality of individual switches 110 by turning on the respective individual switch.

In an exemplary embodiment, circuit 100 may further include a plurality of transceiver modules 114. Plurality of transceiver modules 114 may include a first transceiver module 116. In an exemplary embodiment, first transceiver module 116 may include an input node P1, an input node P2, and an output node O1. Input node P1 may be connected to a second electrode 118 of plurality of electrodes 104. Input node P2 may be connected to a third electrode 120 of plurality of electrodes 104. Output node O1 may be connected to processing unit 108. In an exemplary embodiment, processing unit 108 may be configured to control data transfer through plurality of transceiver modules 114. Transceiver module 116 may be configured to receive data from second electrode 118 and third electrode 120. In another exemplary embodiment, first electrode 112 may be the same (or may have similar properties) as second electrode 120.

In an exemplary embodiment, circuit 100 may further include an adder module 122. Adder module 122 may be configured to receive data from an output node DRL1 of first transceiver module 116 and receive data from an output node DRL2 of a second transceiver module 124 of plurality of transceiver modules 114. In an embodiment, a sum of data on output node DRL1 and data on output node DRL2 may be loaded to an output node SUM of adder module 122.

Figure 2:
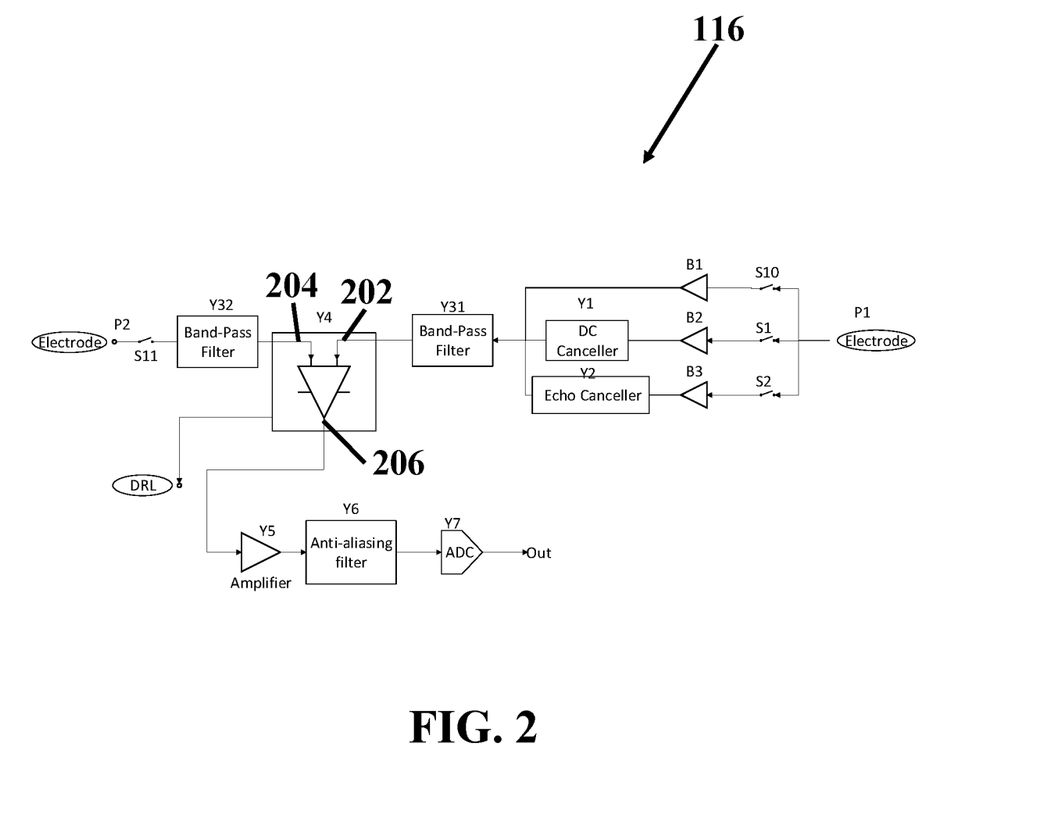
FIG. 2 shows a schematic of a transceiver module, consistent with one or more embodiments of the present disclosure.

FIG. 2 shows a schematic of a transceiver module, consistent with one or more embodiments of the present disclosure. In an exemplary embodiment, first transceiver module 116 may further include a DC canceller module Y1, an echo canceller module Y2, a first band-pass filter Y31, a second band-pass filter Y32, a differential amplifier Y4, an amplifier Y5, an anti-aliasing filter Y6, an analog-to-digital converter (ADC) Y7, and an output node OUT. In an exemplary embodiment, DC canceller module Y1 may be connected to input node P1 through a buffer B2 and a switch S1. Switch S1 may be controlled by processing unit 108. DC canceller module Y1 may be configured to suppress DC data of input node P1. In an embodiment, echo canceller module Y2 may be connected to input node P1 through a buffer B3 and a switch S2. Switch S2 may be controlled by processing unit 108. Echo canceller module Y2 may be configured to suppress echoes of AC data of input node P1. In an exemplary embodiment, first band-pass filter Y31 may be connected to input node P1 through a buffer B1 and a switch S10. Switch S10 may be controlled by processing unit 108. Outputs of DC canceller module Y1 and echo canceller module Y2 may be connected to an input node of first band-pass filter. In an exemplary embodiment, second band-pass filter Y32 may be connected to input node P2 through a switch S11. Switch S11 may be controlled by processing unit Y32. In an exemplary embodiment, differential amplifier Y4 may include a first differential input node 202, a second differential input node 204, a differential output node 206, and a differential ground node DRL. In an embodiment, the differential input node 202 may be connected to an output of first band-pass filter Y31. Second differential input node 204 may be connected to an output of second band-pass filter Y32. Differential ground node DRL may be connected to an output node DRL1. In an exemplary embodiment, differential amplifier Y4 may be configured to load an amplification of a difference between data on first differential input node 202 and data on second differential input node 204 to differential output node 206. In an exemplary embodiment, amplifier Y5 may be configured to amplify data of differential output node 206. Anti-aliasing filter Y6 may be connected to amplifier Y5 output. ADC Y7 may be connected to an output of anti-aliasing filter Y6. Output node OUT may be connected to an output of ADC Y7.

Figure 3:
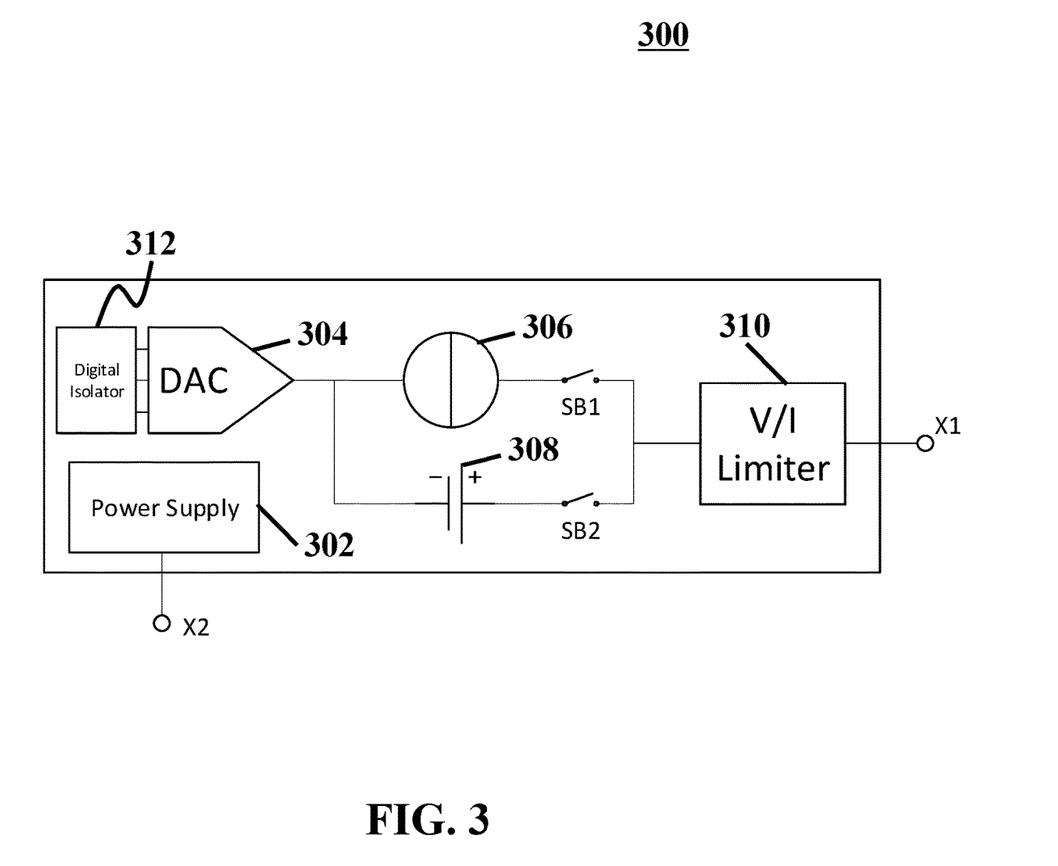
FIG. 3 shows a schematic of an electrical stimulator, consistent with one or more embodiments of the present disclosure.

FIG. 3 shows a schematic of an electrical stimulator 300 of plurality of electrical stimulators 102, consistent with one or more embodiments of the present disclosure. In an exemplary embodiment, electrical stimulator 300 may include a power supply 302, a digital to analog converter (DAC) 304, a current source 306, a voltage source 308, a node X1, and a node X2. In an embodiment, DAC 304 may be configured to generate an amplitude and a frequency of the electrical signal. Current source 306 may be connected to an output node of DAC 304. The voltage source 308 may be connected to the output node of DAC 304. Node X1 may be connected to current source 306 through a voltage/current limiter 310 and a switch SB1, and may be connected to voltage source 308 through voltage/current limiter 310 and a switch SB2. In an exemplary embodiment, voltage/current limiter 310 and switches SB1 and SB2 may be controlled by processing unit 108. Node X2 may be connected to power supply 302.

In an exemplary embodiment, processing unit 108 may be configured to provide a digital amplitude and a digital frequency of the electrical signal to DAC 304. In an exemplary embodiment, power supply 302 may include an isolated DC power supply.

In an exemplary embodiment, the electrical stimulator may further include a digital data isolator 312. Digital data isolator 312 may be configured by processing unit 108 to provide a digital amplitude and a digital frequency of the electrical signal to DAC 304.

Figure 4:
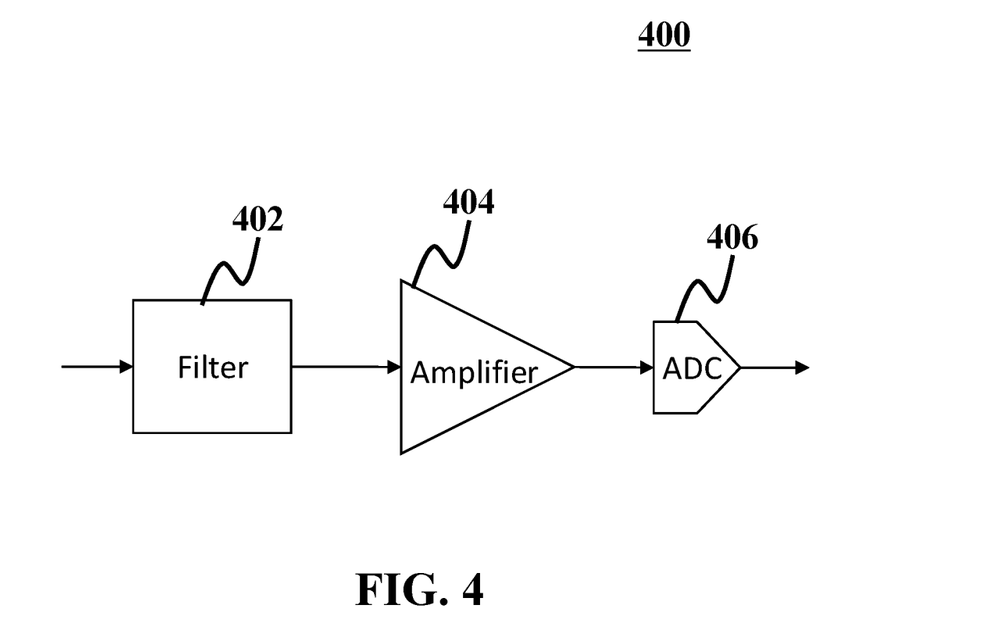
FIG. 4 shows a schematic of an amplification unit, consistent with one or more embodiments of the present disclosure.

FIG. 4 shows a schematic of an amplification unit, consistent with one or more embodiments of the present disclosure. Referring to FIGS. 1 and 4, in an exemplary embodiment, the circuit may further include an amplification module 400. Amplification module 400 may include a filter 402, an amplifier 404, and analog to digital converter (ADC) 406. In an exemplary embodiment, filter 402, amplifier 404, and ADC 406 may be connected in series. Amplification module 400 may be configured to provide a path between first electrode 112 or second electrode 118 and an input of processing unit 108.

In an exemplary embodiment, processing unit 108 may be further configured to calculate an electrical impedance by measuring voltage and current values of first electrode 112 or second electrode 118 through the amplification module. In an exemplary embodiment, plurality of electrodes 104 may include an electroencephalography (EEG) electrode connected to a head of a patient.

Figure 5:
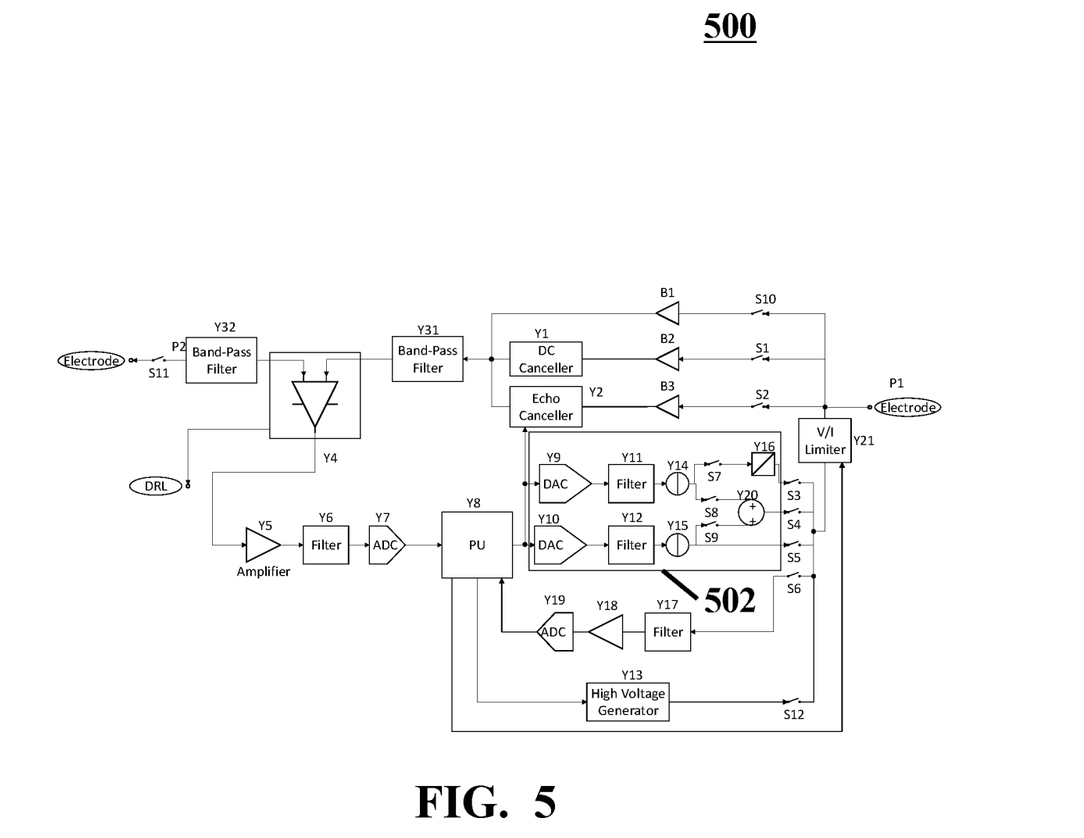
FIG. 5 shows a schematic of a circuit for electrical stimulation of brain, consistent with one or more embodiments of the present disclosure.

FIG. 5 shows a schematic of a circuit 500 for electrical stimulation of a brain, consistent with one or more embodiments of the present disclosure. In an exemplary embodiment, the circuit 500 may include a differential amplifier Y4, an electrical stimulator 502, and a processing unit Y8. In an embodiment, differential amplifier Y4 may be configured to amplify a difference between data on a node P1 and a node P2. Electrical stimulator 502 may be configured to load an electrical signal on node P1. Processing unit Y8 may be configured to generate an amplitude and a frequency of the electrical signal. Referring to FIG. 1, in an exemplary embodiment, node P1 may be connected to second electrode 118.

In an exemplary embodiment, electrical stimulator 502 may include a first digital to analog converter (DAC) Y9, a main current source Y14, a current dependent voltage source Y16, a second digital to analog converter (DAC) Y10, an auxiliary current source Y15, and an adder unit Y20. In an embodiment, first DAC Y9 may be configured to receive a first pair of digital values for the amplitude and the frequency from processing unit Y8, and convert the first pair of digital values to a first pair of analog values. Main current source Y14 may be configured to generate a main electric current according to the first pair of analog values. Current dependent voltage source Y16 may be connected to the main current source through a switch S7. Switch S7 may be controlled by processing unit Y8. Second DAC Y10 may be configured to receive a second pair of digital values for the amplitude and the frequency from processing unit Y8, and convert the second pair of digital values to a second pair of analog values. Auxiliary current source Y15 may be configured to generate an auxiliary electric current according to the second pair of analog values. In an embodiment, Adder unit Y20 may include a first adder input, a second adder input, and an adder output. The first adder input may be connected to main current source Y14 through a switch S8. Switch S8 may be controlled by processing unit Y8. The second adder input may be connected to auxiliary current source Y15 through a switch S9. Switch S9 may be controlled by processing unit Y8. In an exemplary embodiment, adder unit Y20 may be configured to load a sum of the first adder input and the second adder input to the adder output. Main current source Y14 may be connected to processing unit Y8 through first DAC Y9 and a first filter Y11. Auxiliary current source Y15 may be connected to processing unit Y8 through second DAC Y10 and a second filter Y12. An output of current dependent voltage source Y16 may be connected to node P1 through a switch S3 and a voltage/current limiter Y21. Switch S3 and voltage/current limiter Y21 may be controlled by processing unit Y8. The adder output may be connected to node P1 through a switch S4 and voltage/current limiter Y21. Switch S4 may be controlled by processing unit Y8. An output of auxiliary current source Y15 may be connected to node P1 through a switch S5 and the voltage/current limiter Y21. Switch S5 may be controlled by processing unit Y8.

In an embodiment, circuit 500 may further include a DC canceller module Y1, an echo canceller module Y2, a first band-pass filter Y31, a second band-pass filter Y32, a first amplifier Y5, an anti-aliasing filter Y6, and a first analog-to-digital converter (ADC) Y7. In an exemplary embodiment, DC canceller module Y1 may be connected to input node P1 through a buffer B2 and a switch S1. Switch S1 may be controlled by processing unit Y8. DC canceller module Y1 may be configured to suppress DC data of input node P1. In an embodiment, echo canceller module Y2 may be connected to input node P1 through a buffer B3 and a switch S2. Switch S2 may be controlled by the processing unit. Echo canceller module may be configured by processing unit Y8 to suppress echoes of AC data of input node P1. In an exemplary embodiment, first band-pass filter Y31 may be connected to input node P1 through a buffer B1 and a switch S10. Switch S10 may be controlled by processing unit Y8. Outputs of DC canceller module Y1 and echo canceller module Y2 may be connected to an input node of first band-pass filter Y31. An output of first band-pass filter Y31 may be connected to a first differential input node of the differential amplifier. Second band-pass filter Y32 may be connected to input node P2 through a switch S11. Switch S11 may be controlled by processing unit Y8. An output of second band-pass filter Y32 may be connected to a first differential input node of differential amplifier First amplifier Y5 may be configured to amplify an output of the differential amplifier Y4. Anti-aliasing filter Y6 may be connected to the amplifier output. First ADC Y7 may be connected to an output of anti-aliasing filter Y6. An output of first ADC Y7 may be loaded to processing unit Y8.

In an exemplary embodiment, processing unit Y8 may be further configured to receive voltage and current values of second electrode 118 from node P1 through voltage/current limiter Y21, a switch S6, a third filter Y17, a second amplifier Y18, and a second analog-to-digital converter (ADC) Y19, and calculate an electrical impedance by processing the voltage and the current values of second electrode 118.

In an embodiment, processing unit Y8 may be further configured to generate a high voltage by a high-voltage generator module Y13, and load the high voltage on node P1 through a switch S12. Switch S12 may be controlled by the processing unit.

In an exemplary embodiment, differential amplifier Y4 may include an instrumentation amplifier. A ground node of the instrumentation amplifier may be connected to a drive right leg (DRL) circuit.

Referring again to FIG. 1, in an embodiment, node P2 may be connected to third electrode 120 of plurality of electrodes 104 through a switch S11. Switch S11 may be controlled by processing unit Y8.

Figure 6:
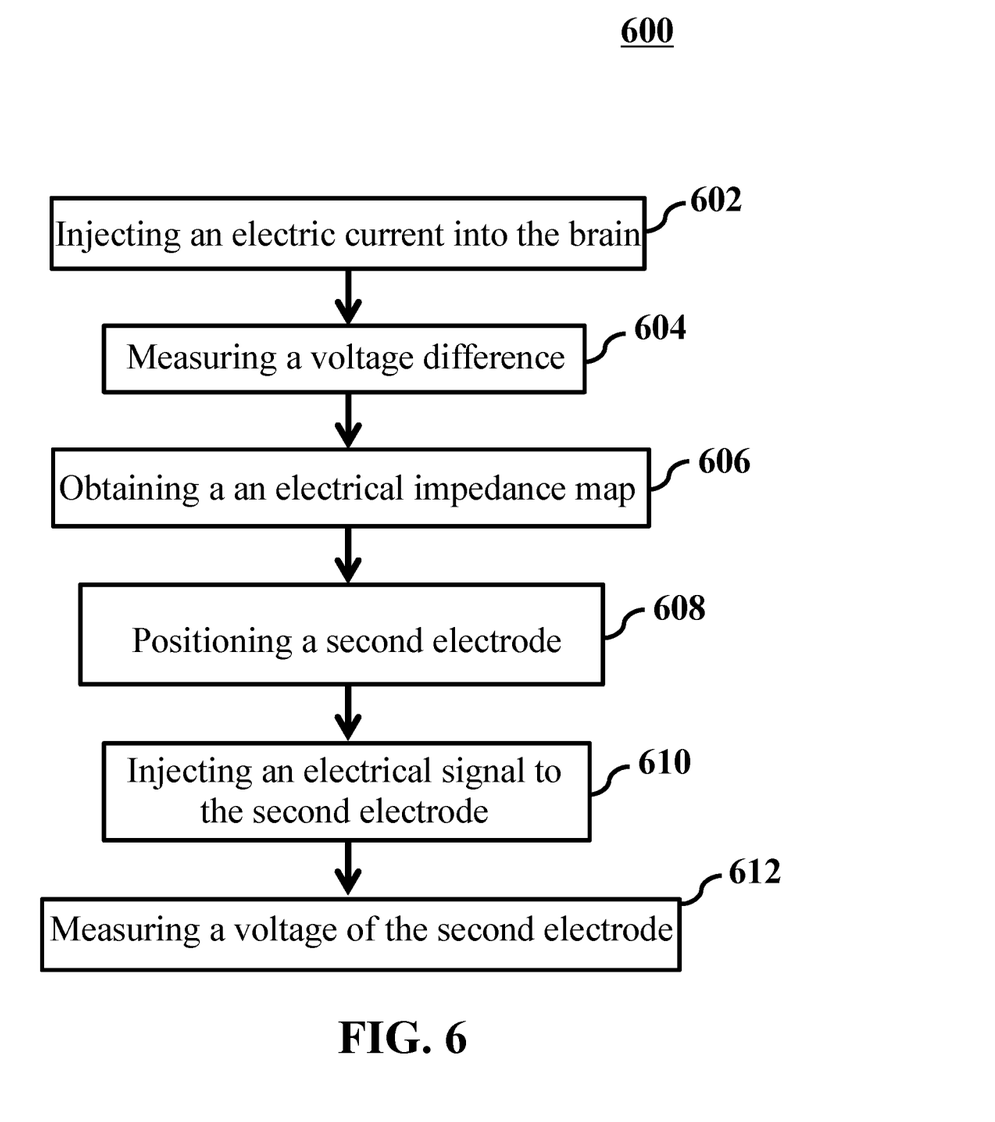
FIG. 6 shows a flowchart of a method for electrical stimulation of brain, consistent with one or more embodiments of the present disclosure.

FIG. 6 shows a flowchart of an exemplary method 600 for electrical stimulation of a brain, consistent with one or more embodiments of the present disclosure. Method 600 may include injecting an electric current into the brain through a first electrode of a plurality of electrodes (step 602), measuring a voltage difference between a pair of electrodes of the plurality of electrodes by a transceiver module (step 604), obtaining an electrical impedance map of the brain by an electrical impedance tomography (EIT) imaging process (step 606), positioning a second electrode of the plurality of electrodes on the head of the patient according to the electrical impedance map (step 608), injecting an electrical signal to the second electrode by an electrical stimulator (step 610), and measuring a voltage of the second electrode by the transceiver module (step 612). The plurality of electrodes may be placed on a head of a patient. The electric current may be generated by an electrical stimulator. The transceiver module may be configured to receive data from the pair of electrodes. The electric current and the voltage difference may be used as boundary values in the EIT imaging process. Injecting the electrical signal and measuring the voltage may be performed simultaneously.

Example 1: Multi-Isle HD tDCS/tACS/tRNS (Using Isolated Currents Sources)

This example introduces a High Definition current stimulation system which may be implemented by using electrical stimulators that include two or more common electrodes as a sink or a source on different sets of electrodes. In this example, one side of two or more sets of electrodes are connected to two or more sink/source electrodes (through a crossbar switch) and all other sides of the selected isolated current sources are connected to the desired electrodes. Table 1 shows switch states for the circuit of Example 1 according to FIGS. 1-5.

TABLE 1

| Switch states for the circuit of Example 1 | | | | | | | | | | | | | |
|---|---|---|---|---|---|---|---|---|---|---|---|---|---|
| S1 | S2 | S3 | S4 | S5 | S6 | S7 | S8 | S9 | S10 | S11 | S12 | SB1 | SB2 |
| 0 | 0 | 0 | 0 | 0 | 0 | 0 | 0 | 0 | 0 | 0 | 0 | 1 | 0 |

Example 2: EEG Recording

This Example shows how to use the system as a signal recorder (EEG) without stimulations. Table 2 shows switch states for the circuit of Example 2 according to FIGS. 1-5.

TABLE 2

| Switch states for the circuit of Example 2 | | | | | | | | | | | | | |
|---|---|---|---|---|---|---|---|---|---|---|---|---|---|
| S1 | S2 | S3 | S4 | S5 | S6 | S7 | S8 | S9 | S10 | S11 | S12 | SB1 | SB2 |
| 0 | 0 | 0 | 0 | 1 | 1 | 0 | 0 | 0 | 1 | 1 | 0 | 0 | 0 |

Example 3: EIT Imaging

This example introduces an electrical impedance tomography system. Table 3 shows switch states for the circuit of Example 3 according to FIGS. 1-5.

TABLE 3

| Switch states for the circuit of Example 3 | | | | | | | | | | | | | |
|---|---|---|---|---|---|---|---|---|---|---|---|---|---|
| S1 | S2 | S3 | S4 | S5 | S6 | S7 | S8 | S9 | S10 | S11 | S12 | SB1 | SB2 |
| 0 | 0 | 0 | 0 | 0 | 0 | 0 | 0 | 0 | 1 | 1 | 0 | 0 | 0 |

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments. This is for purposes of streamlining the disclosure, and is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments have been described, the description is intended to be exemplary, rather than limiting and it will be apparent to those of ordinary skill in the art that many more embodiments and embodiments are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A circuit for electrical stimulation of a brain with simultaneous electroencephalography (EEG) recording, the circuit comprising:
   a plurality of electrodes configured to be placed on a head of a patient;
   a plurality of electrical stimulators, each of the plurality of electrical stimulators configured to generate an electrical signal, an electrical stimulator of the plurality of electrical stimulators configured to electrically stimulate the brain of the patient by injecting the electrical signal to the brain through a first electrode of the plurality of electrodes;
   a plurality of transceiver modules, a first transceiver module of the plurality of transceiver modules configured to record an EEG signal of the patient simultaneously with injecting the electrical signal to the brain through the first electrode;
   a crossbar switch comprising a plurality of individual switches; and
   a processing unit configured to provide a connection between the electrical stimulator and the first electrode through an individual switch of the plurality of individual switches by turning on the individual switch,
   wherein the first transceiver module comprises:
      a first input node connected to a second electrode of the plurality of electrodes;
      a second input node connected to a third electrode of the plurality of electrodes;
      a DC canceller module connected to the first input node through a second buffer and a first switch, the first switch configured to be controlled by the processing unit, the DC canceller module configured to suppress DC data of a voltage of the second electrode through the first input node;
      an echo canceller module connected to the first input node through a third buffer and a second switch, the second switch configured to be controlled by the processing unit, the echo canceller module configured to suppress echoes of AC data of the voltage of the second electrode through the first input node;
      a first band-pass filter connected to the first input node through a first buffer and a third switch and configured to receive the voltage of the second electrode through the first input node, wherein:
         the third switch is configured to be controlled by the processing unit; and
         outputs of the DC canceller module and the echo canceller module connected to an input node of the first band-pass filter;
      a second band-pass filter connected to the second input node through a fourth switch and configured to receive a voltage of third electrode through the second input node, the fourth switch configured to be controlled by the processing unit;
      a differential amplifier comprising:
         a first differential input node connected to an output of the first band-pass filter, the first differential input node configured to receive the voltage of the second electrode through the output of the first band-pass filter;
         a second differential input node connected to an output of the second band-pass filter, the second differential input node configured to receive the voltage of the third electrode through the output of the second band-pass filter;
         a differential output node; and
         a differential ground node connected to an output node DRL1,
      wherein the differential amplifier is configured to load an amplification of a difference between data on the first differential input node and data on the second differential input node to the differential output node;
      a first amplifier configured to amplify data of the differential output node;
      an anti-aliasing filter connected to an output of the first amplifier and configured to receive the output of the first amplifier;
      a first analog-to-digital converter (ADC) connected to an output of the anti-aliasing filter and configured to the receive the output of the anti-aliasing filter; and
      an output node OUT connected to an output of the first ADC, the output node OUT configured to load the output of the first ADC to the processing unit.

2. The circuit of claim 1, wherein the first electrode is the same as the second electrode.

3. The circuit of claim 1, wherein the electrical stimulator comprises:
   a power supply;
   a digital to analog converter (DAC) configured to generate an amplitude and a frequency of the electrical signal;
   a current source connected to an output node of the DAC;
   a voltage source connected to the output node of the DAC;
   a first node (X1) connected to the current source through a voltage/current limiter and a first switch (SB1), and connected to the voltage source through the voltage/current limiter and a second switch (SB2), the voltage/current limiter and the switches SB1 and SB2 being controlled by the processing unit; and
   a second node (X2) connected to the power supply.

4. The circuit of claim 3, wherein the processing unit is configured to provide a digital amplitude and a digital frequency of the electrical signal to the DAC.

5. The circuit of claim 3, wherein the power supply includes an isolated DC power supply.

6. The circuit of claim 5, wherein the electrical stimulator further comprises a digital data isolator configured to provide a digital amplitude and a digital frequency of the electrical signal to the DAC.

7. The circuit of claim 1, further comprising an amplification module, the amplification module comprising a filter, a second amplifier, and a second ADC connected in series, the amplification module providing a path between the first electrode and an input of the processing unit.

8. The circuit of claim 7, wherein the processing unit is further configured to calculate an electrical impedance by measuring voltage and current values of the first electrode through the amplification module.

* * * * *